US009016936B2

(12) United States Patent
Bianchessi et al.

(10) Patent No.: US 9,016,936 B2
(45) Date of Patent: Apr. 28, 2015

(54) METHOD OF CALIBRATING A TEMPERATURE SENSOR OF A CHEMICAL MICROREACTOR AND ANALYZER FOR BIOCHEMICAL ANALYSES

(75) Inventors: Marco Angelo Bianchessi, Melzo (IT); Alessandro Cocci, Agrate Brianza (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 625 days.

(21) Appl. No.: 13/338,615

(22) Filed: Dec. 28, 2011

(65) Prior Publication Data

US 2012/0170608 A1   Jul. 5, 2012

(51) Int. Cl.
| | |
|---|---|
| G01K 7/14 | (2006.01) |
| G01K 1/02 | (2006.01) |
| G01K 1/14 | (2006.01) |
| G01K 15/00 | (2006.01) |
| G01N 35/00 | (2006.01) |

(52) U.S. Cl.
CPC .............. *G01K 15/00* (2013.01); *G01K 15/005* (2013.01); *G01N 2035/00346* (2013.01)

(58) Field of Classification Search
CPC .. G01J 5/522; G01J 2005/0048; G01K 15/00; G01K 15/005; G01K 15/007; G01K 17/006
USPC ......... 374/1, 2, 3, 10, 11, 12, 29, 30, 31, 137, 374/141, 100, 102; 422/105, 108, 109, 130, 422/198; 702/85, 99
See application file for complete search history.

(56) References Cited

U.S. PATENT DOCUMENTS

| | | | | |
|---|---|---|---|---|
| 4,838,705 | A * | 6/1989 | Byers et al. ...................... 374/14 |
| 5,295,746 | A * | 3/1994 | Friauf et al. ................... 374/170 |
| 5,616,301 | A * | 4/1997 | Moser et al. ..................... 422/64 |
| 6,616,438 | B2 * | 9/2003 | Burlone et al. ............... 425/144 |
| 6,962,821 | B2 * | 11/2005 | Danssaert et al. ............. 436/501 |
| 7,431,891 | B2 * | 10/2008 | Greve et al. ................... 422/109 |
| 7,691,334 | B2 * | 4/2010 | Onoue ........................... 422/109 |
| 8,246,243 | B2 * | 8/2012 | Atwood et al. .................... 374/1 |
| 8,771,229 | B2 * | 7/2014 | Amirouche et al. .......... 604/153 |
| 8,790,307 | B2 * | 7/2014 | Amirouche et al. .......... 604/151 |
| 8,801,275 | B2 * | 8/2014 | Wu ................................. 374/109 |
| 2003/0190755 | A1 * | 10/2003 | Turner et al. .................... 436/37 |
| 2004/0204884 | A1 | 10/2004 | Cardelius et al. |
| 2005/0089993 | A1 * | 4/2005 | Boccazzi et al. ........... 435/286.2 |
| 2006/0045821 | A1 * | 3/2006 | McKelvy et al. ............. 422/130 |
| 2008/0299013 | A1 * | 12/2008 | Trieu et al. ..................... 422/104 |
| 2010/0145175 | A1 * | 6/2010 | Soldo et al. ................... 600/365 |
| 2010/0285571 | A1 | 11/2010 | Coursey et al. |
| 2014/0275868 | A1 * | 9/2014 | Rule et al. ..................... 600/310 |

FOREIGN PATENT DOCUMENTS

| | | | |
|---|---|---|---|
| EP | 0668500 A3 | * | 6/1998 |
| IT | T020101088 | * | 7/2012 |
| JP | 2009074925 A | | 4/2009 |
| WO | WO 2009123447 A1 | * | 10/2009 |

* cited by examiner

*Primary Examiner* — Gail Kaplan Verbitsky
(74) *Attorney, Agent, or Firm* — Seed IP Law Group PLLC

(57) ABSTRACT

A method of calibrating a temperature sensor of a chemical microreactor envisages: determining an airflow along a path in such a way as to cause a thermal exchange between the airflow and a chemical microreactor, which is provided with an on-board temperature sensor and is set along the path; and detecting a temperature in the airflow downstream of the microreactor, in conditions of thermal equilibrium.

24 Claims, 5 Drawing Sheets

METHOD OF CALIBRATING A TEMPERATURE SENSOR OF A CHEMICAL MICROREACTOR AND ANALYZER FOR BIOCHEMICAL ANALYSES

BACKGROUND

1. Technical Field

The present disclosure relates to a method of calibrating a temperature sensor of a chemical microreactor and an analyzer for biochemical analyses.

2. Description of the Related Art

As is known, the analysis of nucleic acids involves, according to different modalities, preliminary steps of preparation of a specimen of biological material, amplification of the nucleic material contained therein, and hybridization of individual target or reference strands, corresponding to the sequences sought. Hybridization takes place (and the test yields a positive outcome) if the specimen contains strands complementary to the target strands.

At the end of the preparatory steps, the specimen is examined for controlling whether hybridization has taken place (the so-called "detection step").

The preparatory steps that precede amplification can be conducted separately, using purposely provided instrumentation and reagents.

With increasing frequency, at least for the amplification of nucleic material and for the detection step, integrated chemical microreactors are used, which enable various operations to be carried out without having to transfer the material being processed. The microreactors can be provided in monolithic bodies, such as, for example, semiconductor chips, or joining chips of various materials. According to common solutions, for example, some microreactors comprise a first chip, generally made of plastic material, which houses reservoirs or wells possibly connected through microfluidic connections, and a semiconductor chip, on which heaters and temperature sensors are provided.

The microreactors are loaded with biological specimens to be analyzed and are introduced in thermocyclers to carry out biochemical analyses.

A thermocycler is configured to receive microreactors mounted on purposely provided boards and comprises in general at least a control unit, a cooling device, and a detection device.

The control unit can be connected to the microreactor through connectors and, by exploiting the temperature sensors on board the microreactor itself, controls the heaters and the cooling device for carrying out pre-determined thermal cycles.

Once the biochemical processes are completed, the detection device, which is often of an optical type, verifies whether in the specimen processed given substances (for example, given sequences of nucleotides) are present or not. The optical detection exploits in general fluorophores, which, during processing of the specimen, bind selectively to the substances to be detected.

In the execution of thermal cycles that enable performance of the biochemical processes in the microreactor, it is of fundamental importance that the temperature be controlled in an extremely precise way. For this reason, the temperature sensors on board the microreactors are calibrated individually prior to use. Currently, the calibration can be carried out only in the factory, which entails some limitations.

In the first place, the time between calibration and use can be rather long and there is consequently the risk of the characteristics of the sensors being modified.

Likewise, the environmental conditions of use of the microreactors as a rule change with respect to the calibration conditions, and also this can adversely affect the performance levels of the temperature sensors.

In addition, the calibration performed in the factory is in general costly because it uses purposely designed testing instruments and in any case involves rather long times.

BRIEF SUMMARY

Some embodiments of the present disclosure provide a method of calibrating a temperature sensor of a chemical microreactor and an analyzer for biochemical analyses that enable the limitations described to be overcome. According to the present disclosure, a method of calibrating a temperature sensor of a chemical microreactor and an analyzer for biochemical analyses are provided, as defined in Claim 1 and Claim 11, respectively.

BRIEF DESCRIPTION OF THE SEVERAL VIEWS OF THE DRAWINGS

For a better understanding of the disclosure, some embodiments thereof will now be described, purely by way of non-limiting example and with reference to the attached drawings, wherein.

DETAILED DESCRIPTION

Figure 1:
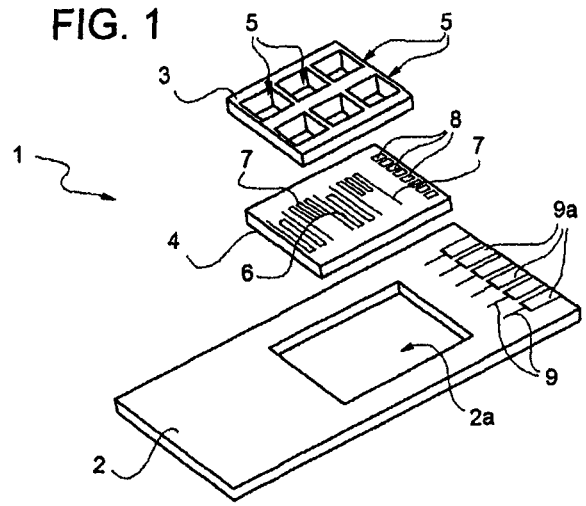
FIG. 1 is an exploded perspective view of a chemical microreactor.

The exploded view of FIG. 1 shows a microreactor 1 for biochemical analyses housed on an electronic printed-circuit board (PCB) 2. More precisely, the PCB 2 has a through opening 2a, where the microreactor 1 is housed.

For simplicity, in what follows reference will be made to microreactors and instrumentation for amplification of nucleic acids by polymerase chain reaction (PCR) and the analysis of the results of the amplification, without this possibly being considered as in any way limiting. What is described hereinafter, in fact, finds advantageous application also in systems designed for execution, and detection of the results, of different biochemical processes, in addition to amplification by means of PCR.

The microreactor 1 comprises a first chip 3, for example made of polymeric material, and a second chip 4, made of semiconductor material, joined to one another.

A plurality of wells 5 are made in the first chip 3 and are configured to receive biological specimens to be analyzed. In one embodiment, the microreactor 1 has been functionalized by fixing DNA probes to the walls of the wells 5. The DNA probes may comprise individual DNA strands containing target sequences of nucleotides to be sought in the biological specimen analyzed.

Heaters 6 and on-board temperature sensors 7 are integrated in the second chip 4. The on-board temperature sensors 7 are of a thermoresistive type. In practice, their resistance varies as a function of the temperature, and hence a reading of the resistance indicates the temperature at a given instant. The second chip 4 projects slightly on one side with respect to the first chip 3, and on the projecting part houses contact pads 8 for connection of the heaters 6 and of the on-board temperature sensors 7 to conductive paths 9 on the PCB 2. Terminals 9a of the paths 9 enable connection of the PCB 2 once it has been inserted in an analyzer.

Figure 2:
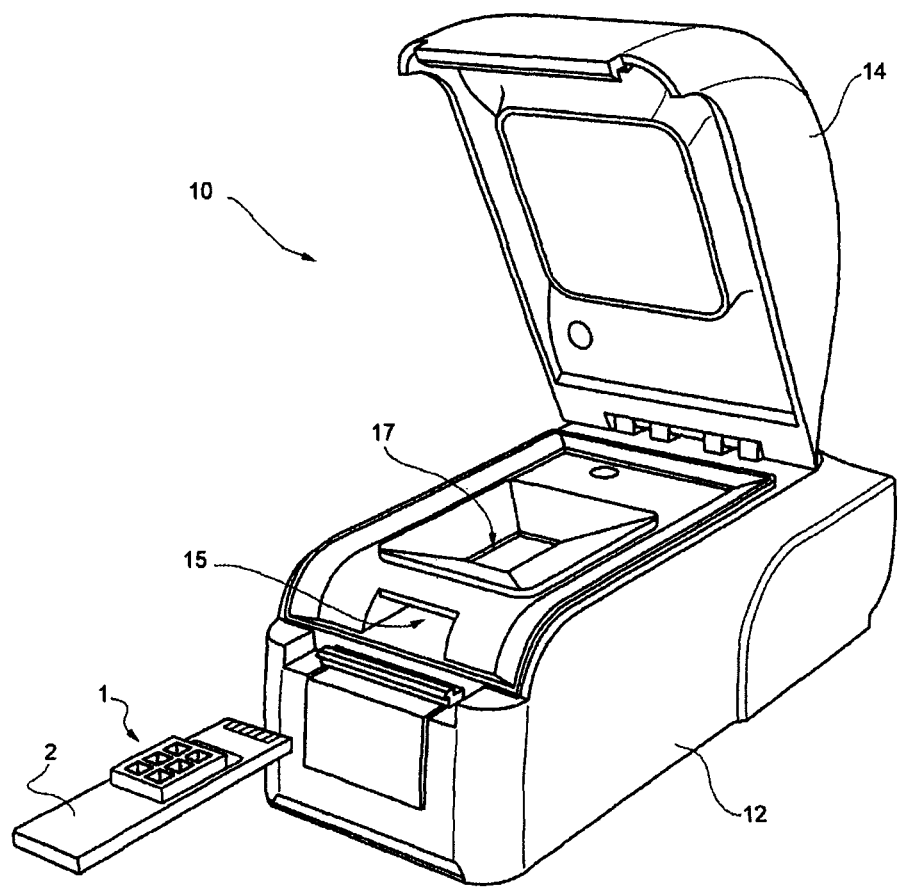
FIG. 2 is a perspective view of an analyzer for biochemical analyses according to an embodiment of the present disclosure.
Figure 3:
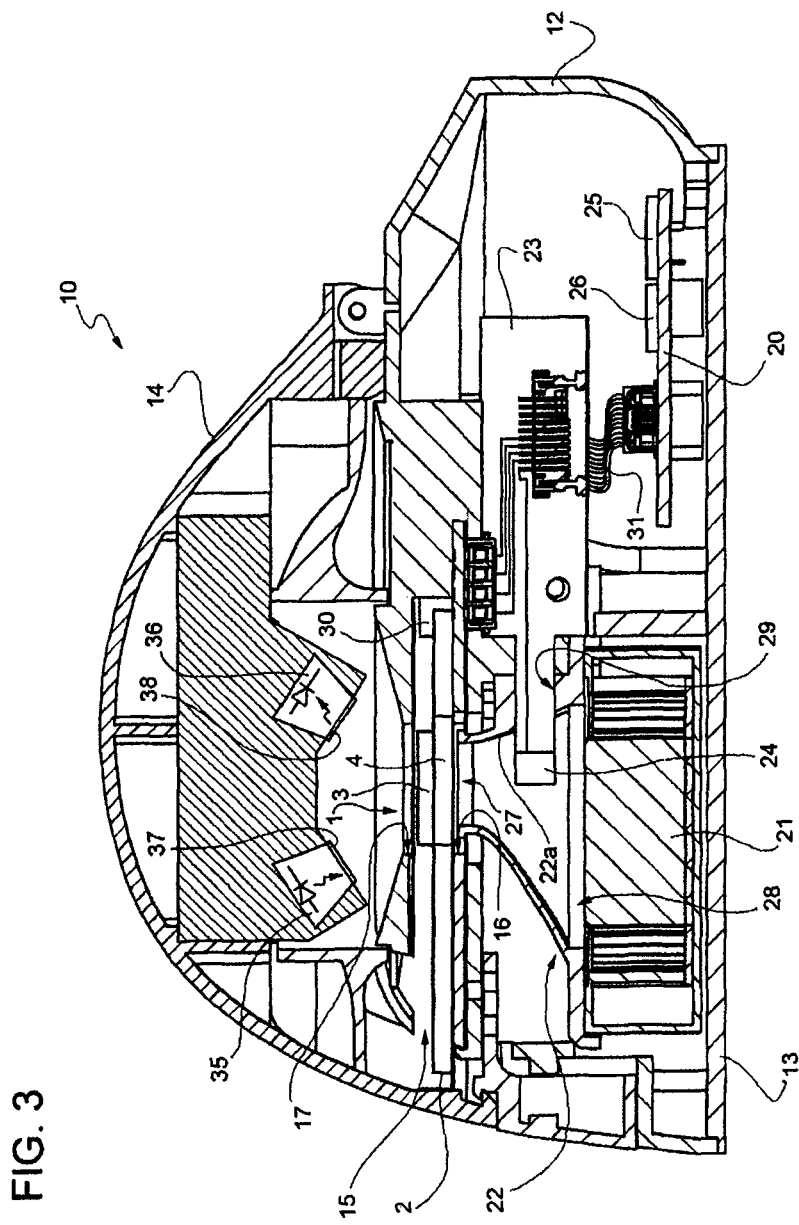
FIG. 3 is a side view, sectioned along a longitudinal plane, of the analyzer of FIG. 2.

As shown in FIGS. 2-3, a real-time PCR analyzer, designated as a whole by the reference number 10, comprises a first shell 12, closed at the bottom by a metal plate 13, and a second shell 14, hinged to the first shell 12. The first shell 12, the metal plate 13, and the second shell 14 define a casing of the analyzer 10.

With reference also to FIG. 3, the first shell 12 has a seat 15 for receiving the microreactor 1 mounted on the PCB 2. The seat 15 is accessible from outside for insertion of the PCB 2 with the microreactor 1 when the second shell 12 is open, in a raised position. In a position corresponding to the position of the microreactor 1 inserted in the seat 15, the first shell 12 has a first window 16 and a second window 17. The first window 16 sets the seat 15 in communication with the inside of the first shell 12, whereas the second window 17 enables observation of the microreactor 1 when the PCB 2 is inserted in the seat 15 and the second shell 14 is lifted.

Housed within the first shell 12 (FIG. 3) are a control board 20, a fan 21, a collector 22, and a sensor board 23, mounted on which is a calibrated temperature sensor 24.

The control board 20 and the fan 21 are fixed to the metal plate 13.

The control board 20 houses a control unit 25, which presides over operation of the analyzer 1, as explained hereinafter, and at least one memory module 26.

In the embodiment described herein, the fan 21 is aligned to the windows 16, 17 and is operable to draw in air through the collector 22. More precisely, a flow of air is drawn in along a path that develops from the seat 15 to the fan 21 through the collector 22, in such a way as to cause a thermal exchange between the airflow and the microreactor 1 arranged in the seat 15.

Figure 4:
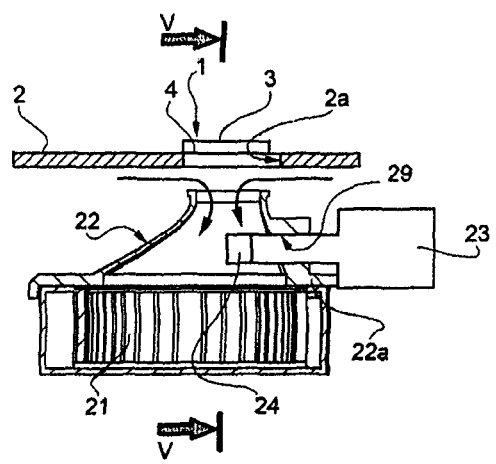
FIG. 4 is a side view sectioned along the plane of trace IV-IV of FIG. 5, simplified and with parts removed for reasons of clarity, of a detail of the analyzer of FIG. 2.
Figure 5:
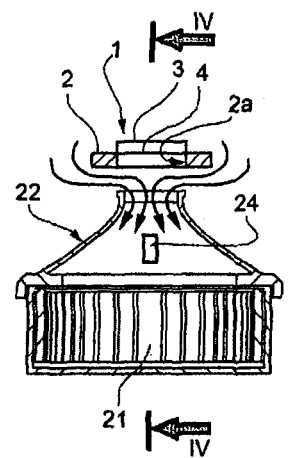
FIG. 5 is a side view sectioned along the plane of trace V-V of FIG. 4, simplified and with parts removed for reasons of clarity, of a detail of the analyzer of FIG. 2.

In greater detail, the collector 22 is bell-shaped and has an inlet opening 27 and an outlet opening 28. The inlet opening 27 is arranged in the proximity of the first window 16 of the seat 15 in such a way that the microreactor 1 is adjacent to the inlet opening 27 and the intake of air into the collector 22 is possible substantially only through the first window 16 itself. The passage section of the collector 22 widens towards the outlet opening 28, which is wider than the inlet opening 27 and is coupled to an inlet of the fan 21. A wall 22a of the collector 22 that faces the sensor board 23 has a slit 29. When the fan 21 is operated, a flow of air is drawn in through the collector 22 and, before reaching the inlet opening 27, laps the microreactor 1 cooling it, as shown in FIGS. 4 and 5. The portion of the microreactor 1 most affected by the thermal exchange with the flow of air drawn in by the fan 21 is the face adjacent to the collector 22, which is exposed through the opening 2a of the PCB 2.

The sensor board 23, as has been mentioned, houses the calibrated temperature sensor 24. In greater detail, the sensor board 23 has a projection, mounted at one end of which is the calibrated temperature sensor 24. The projection of the sensor board 23 is set through the slit 29 in such a way that the end of the projection, together with the calibrated temperature sensor 24, is inside the collector 22. Consequently, when the fan 21 is operated, the calibrated temperature sensor 24 is immersed in the airflow produced, after thermal exchange with the microreactor 1. In addition, the sensor board 23 is provided with: a connector 30, arranged at a closed end of the seat 15 for enabling in use electrical coupling with the PCB 2 and the microreactor 1; and a cable 31 for connection of the calibrated temperature sensor 24 and the PCB 2 to the control unit 25.

The second shell 14 is hinged to the first shell 12 and defines a lid, shaped so as to be coupled in a lightproof way with the first shell 12 and obscure the second window 17. In practice, when the second shell 14 is closed on the first shell 12, the inside of the second shell 14 is substantially inaccessible to light, and the microreactor 1 inserted in the seat 15 is obscured. When the second shell 14 is lifted, the seat 15 is accessible for inserting and removing the PCB 2 with the microreactor 1. When the PCB 2 is in the seat 15, moreover, the microreactor 1 is visible and accessible from outside for enabling operations of introduction of biological specimens to be analyzed.

Housed in the second shell 14 are a light source 35 and a photodetector 36, controlled by the control unit 25.

The light source 35, for example a light-emitting diode (LED), is oriented so as to illuminate the microreactor 1 through the second window 17 and is provided with a narrow-band excitation filter 37, centered around a frequency of excitation of fluorophores used for the analyses in the microreactor 1.

The photodetector 36, for example a photodiode, is arranged so as to receive the radiation emitted by the fluorophores excited by the light coming from the light source 35. The photodetector 36 is provided with an emission filter 38, having a band centered around an emitting frequency of the fluorophores and an amplitude such as to exclude the band of the excitation filter 37.

Figure 6:
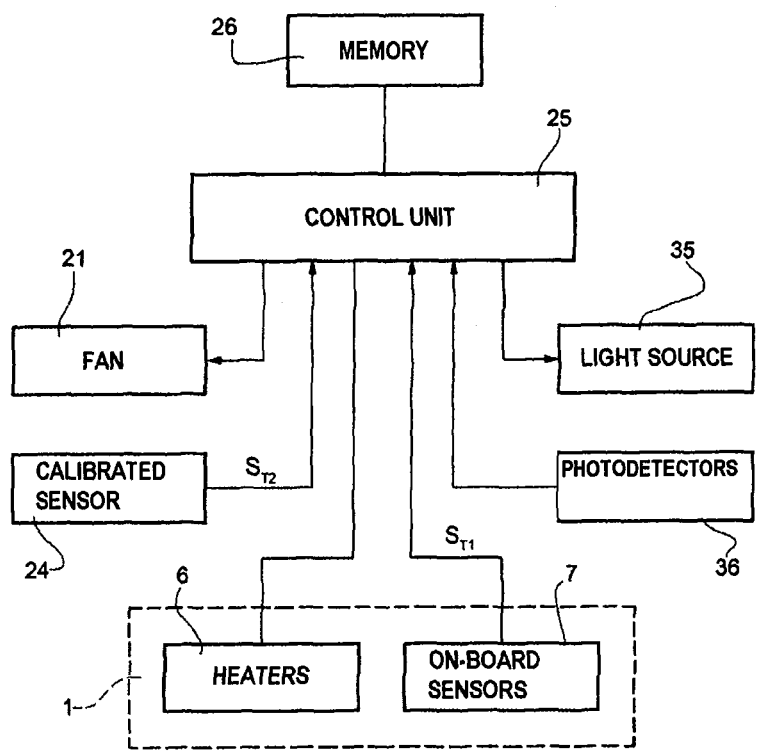
FIG. 6 is a simplified block diagram of the analyzer of FIG. 2.

FIG. 6 shows a block diagram of the analyzer 10 in use, with the microreactor 1 inserted in the slot 15.

Figure 7:
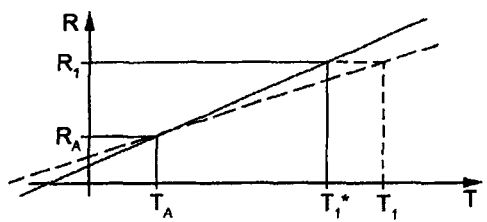
FIG. 7 is a graph that shows a quantity regarding a microreactor that can be used in the analyzer of FIG. 2.

The control unit 25 is coupled to the on-board temperature sensors 7 on the microreactor 1 and with the calibrated temperature sensor 24 that is located in the collector 22 for receiving, respectively, first signals $S_{T1}$, representative of a temperature of the microreactor 1, and a second signal $S_{T2}$, representative of a temperature of the air within the collector 22. More precisely, the first signals $S_{T1}$ indicate the resistance value R of the on-board temperature sensors 7, which depends upon the temperature T, as shown in FIG. 7. From a reading of the values of resistance R, the control unit 25 is able to trace back to the corresponding temperature T, for example using a function stored in the memory module 26.

The control unit 25 is moreover coupled to the heaters 6 and to the fan 21 and is configured to control the temperature of the microreactor 1 according to a temperature profile stored in the memory module 26, during steps of amplification of a biological specimen introduced in the microreactor 1. The control unit 25 actuates alternatively the heaters 6 and the fan 21 on the basis of the first signals $S_{T1}$ supplied by the on-board temperature sensors 7 on the microreactor 1 in such a way that the temperature detected via the first signals $S_{T1}$ will be close to the profile stored in the memory module 26.

In addition, the control unit 25 is configured to carry out a procedure of calibration of the on-board temperature sensors 7 using the second signal $S_{T2}$ supplied by the calibrated temperature sensor 24, as explained in detail hereinafter.

In a step of analysis of the results of the amplification, the control unit 25 actuates the light source 35 and receives detection signals $S_D$ from the photodetector 36.

On the basis of the detection signals $S_D$, the control unit 25 determines the presence or absence of substances in the biological specimen analyzed.

The on-board temperature sensors 7, as mentioned, are of a resistive type; namely, their resistance value R varies as a function of the temperature T, as shown in FIG. 7.

Figure 8:
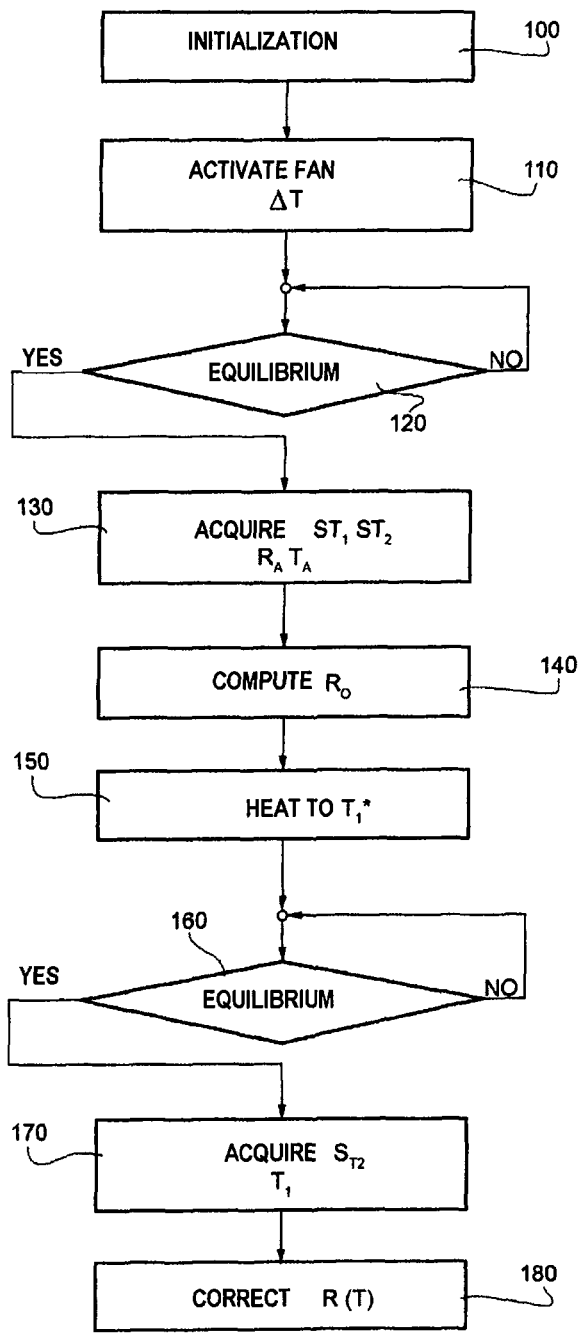
FIG. 8 is a flowchart regarding a method of calibrating a temperature sensor of a chemical microreactor according to an embodiment of the present disclosure.

FIG. 8 illustrates the procedure of calibration of the on-board temperature sensors 7 of the microreactor 1, which is carried out by the control unit 25 using the calibrated temperature sensor 24.

It has been noted that the relation between the resistance R of the on-board temperature sensors 7 and the temperature T is substantially quadratic and, to a fair approximation, can be considered linear:

$$R(T) = R_0(1 + aT + bT^2) \quad (1)$$

and $$R(T) \approx R_0(1 + aT) \quad (2)$$

In the expressions (1) and (2), $R_0$ is the resistance value at 0° C. and depends markedly upon the geometry of the on-board temperature sensors 7. In particular, the parameter $R_0$ is sensitive to the process spread and can vary significantly in devices of one and the same lot.

The parameters a and b are, instead, determined by the material of which the on-board temperature sensors 7 are made and are practically independent of the process conditions. The parameters a and b can hence be stored in the memory module 26. For aluminum, for example, the following values represent a reliable approximation that applies to any device:

$$a = 4.2456 \cdot 10^{-3}$$

$$b = -6.4107 \cdot 10^{-8}$$

After an initialization step (block 100), the control unit 25 activates the fan 21 and actuates for a short period the heaters 6 so as to impress a temperature pulse $\Delta T$ to the microreactor 1 (block 110).

Figure 9:
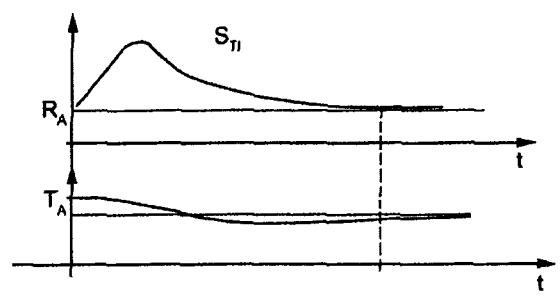
FIG. 9 is a graph that shows a quantity regarding the method of FIG. 8.

Then, with the fan 21 operating, the control unit 25 reads the first signals $S_{T1}$ and the second signal $S_{T2}$ supplied, respectively, by the on-board temperature sensors 7 and by the calibrated temperature sensor 24, until the temperature transients are expired and the thermal equilibrium has been reached at a calibration temperature $T_A$ without intervention of the heaters 6 (block 120, output NO; see also FIGS. 7 and 9). When the thermal equilibrium has been reached (block 120, output YES), the control unit 25 acquires and stores respective values of the first signals $S_{T1}$ and of the second signal $S_{T2}$ (block 130). The first signals $S_{T1}$ indicate a resistance value $R_A$ of the on-board temperature sensors 7 at the calibration ambient temperature $T_A$, whilst the value of the second signal $S_{T2}$ is a calibrated measurement of the calibration ambient temperature $T_A$. The control unit 25 associates the resistance value $R_A$ to the calibration temperature $T_A$, stores the pair $(R_A, T_A)$ in the memory module 26, and determines the value of the parameter $R_0$ on the basis of the expression (block 140):

$$R_0 = R_A/(1 + aT_A + bT_A^2) \quad (3)$$

In one embodiment, the value of the parameter $R_0$ is determined by the control unit 25 on the basis of the approximate expression:

$$R_0 = R_A/(1 + aT_A) \quad (4)$$

The relations (3) and (4) enable determination, in a unique way and with a degree of approximation that in most cases is acceptable, of the relation between the resistance value of the on-board temperature sensors 7, which can be easily measured, and their temperature, which basically corresponds to the temperature of the microreactor 1. In the embodiment described herein, however, further steps for refining the calibration are envisaged.

In particular, the control unit 25, with the fan 21 remaining in operation, actuates the heaters 6 to increase the temperature of the microreactor 1 up to an approximate control-temperature value $T_1^*$. The approximate control-temperature value $T_1^*$ is determined on the basis of a corresponding resistance value $R_1$ of the on-board temperature sensors 7 (block 150).

When the thermal equilibrium has again been reached in the microreactor 1 and in the flow of air drawn in by the fan 21 (block 160, output YES), the control unit 25 acquires a value of the second signal $S_{T2}$ supplied by the calibrated temperature sensor 24 and determines a calibrated control-temperature value $T_1$ (block 170).

Finally (block 180), the control unit 25 corrects the relation between the resistance R of the on-board temperature sensors 7 and the temperature T imposing that the curve defined by the expression (1) or by the expression (2) pass through the point $(R_1, T_1)$.

The steps 150-180 can possibly be repeated for further values of resistance and temperature $(R_2, T_2; \ldots; R_K, T_K)$, if necessary, to refine the calibration further.

In addition, if the microreactor 1 is provided with more than one on-board temperature sensor 7, the calibration is repeated for each sensor present.

The calibration procedure described is based upon the use of a reference measurement obtained by immersing a calibrated temperature sensor in the airflow conveyed by the fan on the microreactor for cooling it. The measurement of temperature with the calibrated sensor is carried out at thermal equilibrium, when the temperature of the airflow is substantially equal to the temperature of the microreactor.

Calibration can thus be carried out in an accurate and reliable way even just prior to use of the microreactor, without any need for procedures carried out in the factory.

Amongst other things, the calibration carried out just prior to use prevents any possible drift that could be caused by the change in environmental conditions and by the time that has elapsed after the procedure carried out in the factory.

The calibration procedure is particularly fast and simple, since, thanks to the observation that the material substantially has no effect on the dependence upon the temperature, at least in one embodiment it is sufficient to determine just one parameter to obtain a sufficiently precise estimate of the temperature of the microreactor.

The method described is moreover suited to being used in portable apparatuses and hence even to being used in field, if need be, as well as obviously in the laboratory.

A further advantage derives from the fact that, in practice, a self-diagnosis procedure is automatically carried out just before starting the analysis. This enables reduction of risks of failure due to various factors, such as, for example, false contacts or possible degradation of the components, in particular of the electrical resistances.

The embodiment described is also advantageous because the flow of air is drawn in through the collector 22, and the calibration temperature is measured within the collector 22 itself In fact, substantially all the air that cools the sensor is conveyed through the collector, and any heat dispersion is minimal, thus improving the measurements.

Figure 10:
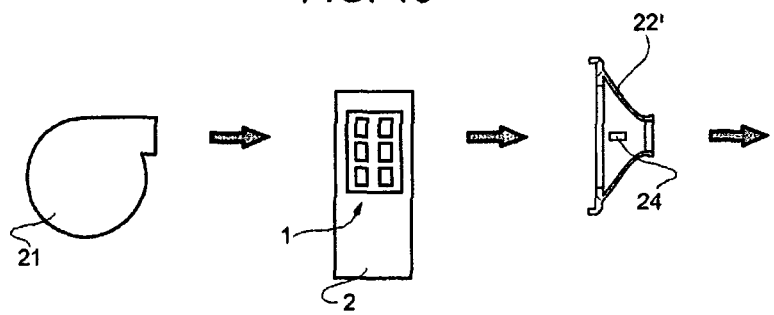
FIG. 10 is a simplified block diagram of an analyzer for biochemical analyses according to a different embodiment of the present disclosure.

However, it is not indispensable to use the fan as a suction fan. In a different embodiment, which is represented in FIG. 10, the fan 21 is arranged so as to blow a flow of cooling air towards the microreactor 1 in such a way as to cause a thermal exchange between the airflow and the microreactor 1. In this case, the calibrated temperature sensor 24 is arranged downstream of the microreactor 1 so as to be immersed in the flow of cooling air after interaction with the microreactor 1. The calibrated temperature sensor 24 can advantageously, but not necessarily, be housed inside a collector 22', which prevents dispersion of the airflow.

Finally, it is evident that modifications and variations may be made to the device and to the method described, without thereby departing from the scope of the present disclosure.

In particular, the method and the analyzer described may be used also for microreactors that use temperature sensors different from thermoresistive sensors. For example, a microreactor could use one or more thermocouples. In this case, the thermocouples can be calibrated substantially as explained, by detecting, in conditions of thermal equilibrium and with the fan active, their output voltage (which depends upon the temperature) and the temperature in the airflow produced by the fan (using the calibrated temperature sensor).

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An analyzer for biochemical analyses comprising:
   a control unit;
   a seat configured to receive a chemical microreactor having an on-board temperature sensor;
   a fan configured to be controlled by the control unit and configured to generate a fluid flow along a path, so as to cause thermal exchange between the fluid flow and the microreactor;
   a collector arranged downstream of the seat, and configured to receive the fluid flow after the thermal exchange between the fluid flow and the microreactor; and
   a calibration temperature sensor arranged inside the collector and along the path of the fluid flow, downstream of the seat, the calibration temperature sensor being configured to sense a downstream temperature of the fluid flow downstream of the microreactor.

2. An analyzer according to claim 1, wherein the control unit is configured to:
   be coupled to the microreactor;
   receive a first signal indicative of a temperature-dependent parameter of the on-board temperature sensor;
   receive from the calibration temperature sensor a second signal indicative of the downstream temperature in the fluid flow;
   determine, based on the second signal, the downstream temperature in the fluid flow, in conditions of thermal equilibrium;
   detect, based on the first signal, a calibration value of a temperature-dependent parameter of the on-board temperature sensor in the conditions of thermal equilibrium, while the microreactor is immersed in the fluid flow; and
   determine a calibration parameter of the on-board temperature sensor based on the downstream temperature and on the calibration value of the temperature-dependent parameter.

3. An analyzer according to claim 1, wherein the fan is arranged so as to suck the fluid flow through the collector.

4. An analyzer according to claim 3, wherein the collector has an inlet opening, arranged near the seat, and configured to be near the microreactor when the microreactor is positioned in the seat; and an outlet opening coupled to an inlet of the fan.

5. An analyzer according to claim 4, comprising:
   a shell inside which the seat, fan, collector, and calibrated temperature sensor are arranged; wherein the shell has a window in a position corresponding to the microreactor when the microreactor is within the shell, and the inlet opening of the collector is arranged so that substantially all of the fluid flow is sucked through the window.

6. An analyzer according to claim 1, wherein a passage section of the collector increases toward the outlet opening, which is wider than the inlet opening.

7. An analyzer, comprising:
   a seat configured to receive a microreactor having an on-board temperature sensor;
   a fan configured to generate a fluid flow along a path and cause thermal exchange between the fluid flow and the microreactor;
   a collector arranged downstream of the seat, and configured to receive the fluid flow after the thermal exchange between the fluid flow and the microreactor; and
   a calibration temperature sensor arranged inside the collector and along the path of the fluid flow and near the seat, the calibration temperature sensor being configured to sense a temperature of the fluid flow.

8. An analyzer according to claim 7, comprising a control unit is configured to:
   be coupled to the microreactor;
   receive a first signal indicative of a temperature-dependent parameter of the on-board temperature sensor;
   receive from the calibration temperature sensor a second signal indicative of the temperature of the fluid flow;
   determine, based on the second signal, the temperature of the fluid flow, in conditions of thermal equilibrium;
   detect, based on the first signal, a calibration value of a temperature-dependent parameter of the on-board temperature sensor in the conditions of thermal equilibrium, while the microreactor is immersed in the fluid flow; and
   determine a calibration parameter of the on-board temperature sensor based on the temperature of the fluid flow and on the calibration value of the temperature-dependent parameter.

9. An analyzer according to claim 7, wherein the collector has an inlet opening, arranged near the seat, and configured to be near the microreactor when the microreactor is positioned in the seat; and an outlet opening coupled to an inlet of the fan.

10. An analyzer according to claim 7, comprising:
    a shell inside which the seat, fan, collector, and calibrated temperature sensor are arranged; wherein the shell has a window in a position corresponding to the microreactor when the microreactor is within the shell, and the inlet opening of the collector is arranged so that substantially all of the fluid flow is sucked through the window.

11. An analyzer according to claim 7, wherein a passage section of the collector increases toward the outlet opening, which is wider than the inlet opening.

12. A method, comprising:
receiving, in a seat of an analyzer, a chemical microreactor having an on-board temperature sensor;
generating, with a fan of the analyzer, a fluid flow along a path, so as to cause thermal exchange between the fluid flow and the microreactor;
receiving, at a collector arranged downstream of the seat, the fluid flow after the thermal exchange between the fluid flow and the microreactor; and
sensing a downstream temperature of the fluid flow downstream of the microreactor using a calibration temperature sensor of the analyzer arranged inside the collector and along the path of the fluid flow, downstream of the seat.

13. The method according to claim 12, comprising:
coupling a control unit to the microreactor;
receiving at the control unit a first signal indicative of a temperature-dependent parameter of the on-board temperature sensor;
receiving at the control unit from the calibration temperature sensor a second signal indicative of the temperature of the fluid flow;
determining at the control unit, based on the second signal, the temperature of the fluid flow, in conditions of thermal equilibrium;
detecting at the control unit, based on the first signal, a calibration value of a temperature-dependent parameter of the on-board temperature sensor in the conditions of thermal equilibrium, while the microreactor is immersed in the fluid flow; and
determining at the control unit a calibration parameter of the on-board temperature sensor based on the temperature of the fluid flow and on the calibration value of the temperature-dependent parameter.

14. The method according to claim 12, wherein:
receiving at the collector includes receiving the fluid flow at an inlet opening of the collector, the inlet opening being arranged near the seat and near the microreactor when the microreactor is positioned in the seat; and
generating the fluid flow includes generating fluid flow at an inlet of the fan coupled to an outlet of the collector.

15. A method comprising:
receiving, in a seat of an analyzer, a chemical microreactor having an on-board temperature sensor;
generating, with a fan of the analyzer, a fluid flow along a path, so as to cause thermal exchange between the fluid flow and the microreactor;
sensing a downstream temperature of the fluid flow downstream of the microreactor using a calibration temperature sensor of the analyzer arranged along the path of the fluid flow, downstream of the seat;
detecting a calibration value of a temperature-dependent parameter of the on-board temperature sensor in thermal equilibrium conditions, while the microreactor is immersed in the fluid flow; and
determining a calibration parameter of the on-board temperature sensor based on the temperature sensed in the fluid flow and on the calibration value of the temperature-dependent parameter.

16. The method according to claim 15, comprising applying a temperature pulse to the microreactor before sensing the temperature and detecting the calibration value of the temperature-dependent parameter.

17. The method according to claim 15, comprising heating the microreactor up to an approximated temperature control value.

18. The method according to claim 17, wherein heating the microreactor up to the approximated temperature control value comprises determining the approximated temperature control value through the on-board temperature sensor of the microreactor.

19. The method according to claim 18, comprising determining a calibrated temperature control value in the fluid flow sucked in conditions of thermal equilibrium, after reaching the approximated temperature control value.

20. The method according to claim 19, comprising correcting the calibration parameter of the on-board temperature sensor based on the calibrated temperature control value.

21. An analyzer, comprising:
a seat configured to receive a microreactor having an on-board temperature sensor;
a fan configured to generate a fluid flow along a path and cause thermal exchange between the fluid flow and the microreactor;
a calibration temperature sensor arranged along the path of the fluid flow and near the seat, the calibration temperature sensor being configured to sense a temperature of the fluid flow; and
a control unit configured to:
be coupled to the microreactor;
receive a first signal indicative of a temperature-dependent parameter of the on-board temperature sensor;
receive from the calibration temperature sensor a second signal indicative of the temperature of the fluid flow;
determine, based on the second signal, the temperature of the fluid flow, in conditions of thermal equilibrium;
detect, based on the first signal, a calibration value of a temperature-dependent parameter of the on-board temperature sensor in the conditions of thermal equilibrium, while the microreactor is immersed in the fluid flow; and
determine a calibration parameter of the on-board temperature sensor based on the temperature of the fluid flow and on the calibration value of the temperature-dependent parameter.

22. The analyzer of claim 21, further comprising:
a light source configured to illuminate the microreactor while the microreactor is positioned on the seat; and
a photodetector configured to receive radiation emitted from the microreactor in response to the microreactor being illuminated by the light source.

23. A method, comprising:
receiving, in a seat of an analyzer, a chemical microreactor having an on-board temperature sensor;
generating, with a fan of the analyzer, a fluid flow along a path, so as to cause thermal exchange between the fluid flow and the microreactor;
sensing a downstream temperature of the fluid flow downstream of the microreactor using a calibration temperature sensor of the analyzer arranged along the path of the fluid flow, downstream of the seat;
coupling a control unit to the microreactor;
receiving at the control unit a first signal indicative of a temperature-dependent parameter of the on-board temperature sensor;
receiving at the control unit from the calibration temperature sensor a second signal indicative of the temperature of the fluid flow;
determining at the control unit, based on the second signal, the temperature of the fluid flow, in conditions of thermal equilibrium;
detecting at the control unit, based on the first signal, a calibration value of a temperature-dependent parameter of the on-board temperature sensor in the conditions of thermal equilibrium, while the microreactor is immersed in the fluid flow; and determining at the control unit a calibration parameter of the on-board temperature sensor based on the temperature of the fluid flow and on the calibration value of the temperature-dependent parameter.

24. The method according to claim 23, comprising:

detecting a calibration value of a temperature-dependent parameter of the on-board temperature sensor in thermal equilibrium conditions, while the microreactor is immersed in the fluid flow; and determining a calibration parameter of the on-board temperature sensor based on the temperature sensed in the fluid flow and on the calibration value of the temperature-dependent parameter.

* * * * *

UNITED STATES PATENT AND TRADEMARK OFFICE
CERTIFICATE OF CORRECTION

| | | |
|---|---|---|
| PATENT NO. | : 9,016,936 B2 | Page 1 of 1 |
| APPLICATION NO. | : 13/338615 | |
| DATED | : April 28, 2015 | |
| INVENTOR(S) | : Marco Angelo Bianchessi et al. | |

It is certified that error appears in the above-identified patent and that said Letters Patent is hereby corrected as shown below:

ON THE TITLE PAGE

Item (30):
--ITALY TO2010A001088 12/30/2010-- has been omitted from the issued patent Signed and Sealed this
Nineteenth Day of January, 2016

Michelle K. Lee
*Director of the United States Patent and Trademark Office*